United States Patent [19]

Lafon

[11] Patent Number: 4,980,377
[45] Date of Patent: Dec. 25, 1990

[54] 1-(AMINOPHENYL)-2-AMINOPROPANONE DERIVATIVES

[75] Inventor: Louis Lafon, Paris, France
[73] Assignee: Laboratoire L. Lafon, Masion Alfort, France
[21] Appl. No.: 270,627
[22] Filed: Nov. 14, 1988

Related U.S. Application Data

[63] Continuation-in-part of Ser. No. 765,218, Aug. 13, 1985, abandoned.

[30] Foreign Application Priority Data

Aug. 20, 1984 [FR] France .............................. 84 12962
Aug. 9, 1985 [EP] European Pat. Off. ........ 85401624.3

[51] Int. Cl.⁵ .................. A61K 31/135; C07C 225/22
[52] U.S. Cl. .................................... 514/649; 514/212;
514/227.5; 514/238.8; 514/255; 514/331;
514/428; 544/59; 544/165; 544/392; 544/399;
544/404; 544/410; 546/235; 548/566; 564/342;
564/343; 564/345
[58] Field of Search ...................... 564/343, 345, 342;
514/649

[56] References Cited

U.S. PATENT DOCUMENTS

| 2,128,255 | 8/1938 | Krzikalla et al. ..................... 564/342 |
| 3,536,712 | 10/1970 | Keck et al. ........................... 564/363 |
| 3,772,275 | 11/1973 | Hernestam et al. . | |
| 3,819,706 | 6/1974 | Mehta ................................. 564/345 |
| 4,119,710 | 10/1978 | Engelhardt et al. ................ 564/363 |
| 4,282,206 | 8/1981 | Warner, Jr. et al. . | |
| 4,393,078 | 7/1983 | Peck ................................... 514/649 |

FOREIGN PATENT DOCUMENTS 658735 3/1963 Canada ............................... 564/343
785988 11/1957 United Kingdom .
1180890 2/1970 United Kingdom .

OTHER PUBLICATIONS

Chemical Abstracts, vol. 40, No. 7, Apr. 10, 1946.

Primary Examiner—Glennon H. Hollrah
Assistant Examiner—Scott C. Rand
Attorney, Agent, or Firm—Wegner, Cantor, Mueller & Player

[57] ABSTRACT

The present invention relates to the preparation of new 1-(aminophenyl)-2-aminopropanone derivatives of the general formula:

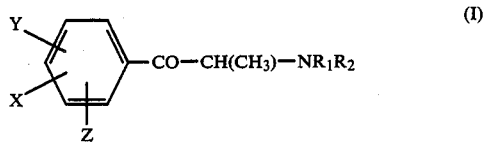

in which X is $NH_2$, Y is H or a halogen atom, Z is H or a halogen atom, $R_1$ is $C_1$-$C_4$ alkyl or $C_3$-$C_6$ cycloalkyl and $R_2$ is H or $C_1$-$C_4$ alkyl, or $R_1$ and $R_2$, taken together, can form, with the nitrogen atom to which they are bonded, a heterocyclic group selected from the group consisting of the pyrrolidino, morpholino, thiomorpholino, piperidino, hexamethyleneimino, piperazino, 4-methyl-piperazino, 4-($\beta$-hydroxyethyl)piperzaino, 4-phenylpiperazino and 4-(p-chlorophenyl)piperazino groups, and addition salts thereof.

These new derivatives are useful as pharmaceuticals. They are obtained by deacetylation of the corresponding acetylated products.

7 Claims, No Drawings

1-(AMINOPHENYL)-2-AMINOPROPANONE DERIVATIVES

CROSS REFERENCE

This patent application is a continuation-in-part application of a prior U.S. patent application Ser. No. 765,218 filed on Aug. 13, 1985, abandoned.

It comprises all the elements disclosed in said prior U.S. patent application and new elements, namely comparison data with compounds according to the prior art teaching.

FIELD OF THE INVENTION

The present invention relates to the preparation of new 1-(aminophenyl)-2-aminopropanone derivatives. These new derivatives are useful in therapy, especially as antidepressants for the central nervous system (CNS), vasodilators and/or immunostimulants.

PRIOR ART

It is known that (aminophenyl)aminoalkanone derivatives have already been described. 1-(4-aminophenyl)-4-morpholinobutanone, 1-(4-aminophenyl)-4-(3-methylmorpholinyl)butanone and 1-(4-aminophenyl)-4-(3-tert.-butylmorpholinyl)butanone are known in particular from patent documents FR-A-No. 2 035 155 and U.S. Pat. No. 3,772,275 as selective inhibitors of monoamine oxidase. 1-(4-Amino-3-chlorophenyl)-2-(3-methoxypropylamino) propanone hydrochloride (cf. Example 44) and 1-(4-amino-3-bromophenyl)2-(2-ethylpiperidino)propanone (cf. Example 45) are also known from patent document GB-A-No. 1 180 890 as synthesis intermediates in the preparation of corresponding propanol compounds, said corresponding propanol compounds being presented as having analgesic properties.

U.S. Pat. No. 4,282,206 discloses the use of 1-(4-aminophenyl)-2-morpholinylethanone as a substance protecting human skin from ultraviolet radiation.

To be precise U.S. Pat. No. 3,772,275, which is cited hereinabove, relates to butyrophenone derivatives of the formula

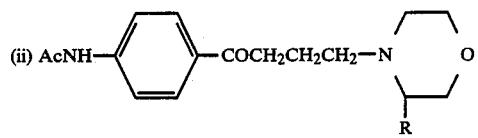

in which R is H or $C_1$–$C_4$ alkyl group, which inhibit monoamine oxydase and are presented as useful as antidepressants, and which are prepared according to the following reaction schemes (i) 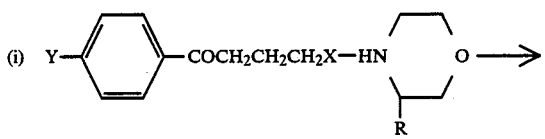

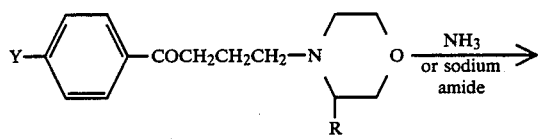

-continued $T_0$ or (ii) 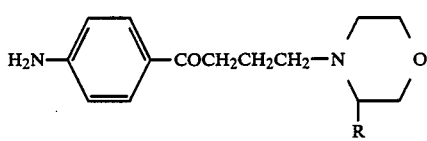

wherein Y is a halogen atom.

OBJECT OF THE INVENTION

It has just been found that the 1-(aminophenyl)-2-aminopropanone derivatives according to the invention, which are structurally different from the above-mentioned derivatives, have valuable therapeutic properties. The new derivatives according to the invention are all active on the CNS and have antidepressant effects in particular. In addition to these antidepressant effects common to all these derivatives, it is found that the said derivatives can have beneficial psychostimulant, immunological and/or cardiovascular effects, as indicated below.

Moreover the new derivatives according to the invention, unlike the prior art compounds, do not exhibit any teratogenic action.

The new derivatives according to the invention are selected from the group consisting of:

(a) the 1-(aminophenyl)-2-aminopropanones corresponding to the general formula:

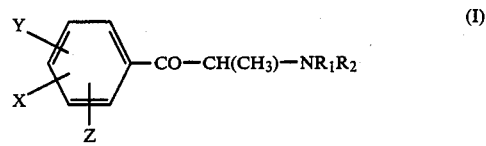

(I)

in which X is $NH_2$, Y is a hydrogen or halogen atom, Z is a hydrogen or halogen atom, $R_1$ is a $C_1$–$C_4$ alkyl group or a $C_3$–$C_6$ cycloalkyl group and $R_2$ is the hydrogen atom or a $C_1$–$C_4$ alkyl group, or $R_1$ and $R_2$, taken together, can form, with the nitrogen atom to which they are bonded, a 5-membered to 7-membered N-heterocyclic group selected from the group consisting of the pyrrolidino, morpholino, thiomorpholino, piperidino, hexamethyleneimino, piperazino, 4-methylpiperazino, 4-($\beta$-hydroxyethyl)piperazino, 4-phenylpiperazino and 4-(p-chlorophenyl)piperazino groups; and (b) addition salts thereof.

DETAILED DISCLOSURE OF THE INVENTION

The groups $CH_3$, $CH_2CH_3$, $CH_2CH_2CH_3$, $CH(CH_3)_2$, $C(CH_3)_3$, $CH(CH_3)CH_2CH_3$, $CH_2CH(CH_3)_2$ and $CH_2CH_2CH_2CH_3$ may be mentioned in particular among the $C_1$–$C_4$ alkyl groups included in the definitions of the groups $R_1$ and $R_2$.

The cyclopropyl, cyclopentyl and cyclohexyl groups may be mentioned in particular among the $C_3$–$C_6$ cycloalkyl groups included in the definition of the group $R_1$.

The N-heterocyclic groups $NR_1R_2$ suitable according to the invention are advantageously saturated. They comprise from 5 to 7 ring members, can include a second heteroatom selected from the group consisting of N, O and S and can be substituted as indicated above.

F, Cl and Br may be mentioned as particularly suitable among the halogen atoms included in the definitions of the groups Y and Z, the preferred halogen atom here being Cl.

Taking account of the definitions given above, the amino group (X=NH₂) on the phenyl group can be in the ortho, meta or para position relative to the carbonyl group. This amino group will preferably be located in the para or meta position.

The preferred groups XYZC₆H₂ are the 4-aminophenyl, 4-amino-3-chlorophenyl, 4-amino-3,5-dichlorophenyl, 3-aminophenyl and 3-amino-4-chlorophenyl groups.

Addition salts are understood here as meaning, on the one hand, the acid addition salts obtained by reacting one of the abovementioned free bases with a mineral or organic acid, and, on the other hand, the ammonium salts. Among the acids which can be used to form salts with the abovementioned free bases, hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluenesulfonic acids may be mentioned in particular. Among the compounds making it possible to obtain ammonium salts, CH₃I and CH₃Cl may be mentioned in particular. In general, the acid addition salts are preferred to the ammonium salts.

A number of compounds according to the invention have been collated in Table I below without in any way implying a limitation. The melting points given are instantaneous melting points determined on a Kofler bench.

TABLE I $$\begin{array}{c}\text{Y} \\ \text{X} \end{array} \!\!\!\!\!\!\bigcirc\!\!\!\!\!\!\begin{array}{c} \\ \text{Z}\end{array}\!\!\!\!\!\!-CO-CH(CH_3)-NR_1R_2$$

| PRODUCT | CODE NO. | X | Y | Z | NR₁R₂ | M.p. (°C.) |
|---|---|---|---|---|---|---|
| Ex. 1 (a) | CRL 41 153 | 4-NH₂ | H | H | NHCH(CH₃)₂ | 210 |
| Ex. 2 (a) | CRL 41 178 | 4-NH₂ | H | H | NHC(CH₃)₃ | 250 (d) |
| Ex. 3 (b) | CRL 41 194 | 4-NH₂ | 3-Cl | 5-Cl | NHCH(CH₃)₂ | (e) |
| Ex. 4 (a) | CRL 41 213 | 4-NH₂ | H | H | NHCH₂CH₂CH₃ | 160 (d) |
| Ex. 5 (a) | CRL 41 218 | 4-NH₂ | H | H | NHCH₃ | 220 (d) |
| Ex. 6 (b) | CRL 41 221 | 4-NH₂ | 3-Cl | H | NHCH(CH₃)₂ | (e) |
| Ex. 7 (a) | CRL 41 222 | 4-NH₂ | H | H | pyrrolidin-1-yl | 200 |
| Ex. 8 (a) | CRL 41 225 | 4-NH₂ | H | H | NHCH₂CH₃ | 190 (d) |
| Ex. 9 (a) | CRL 41 233 | 4-NH₂ | H | H | N(CH₃)₂ | 180 (d) |
| Ex. 10 (a) | CRL 41 237 | 4-NH₂ | H | H | morpholin-4-yl | 210 (d) |
| Ex. 11 (a) | CRL 41 241 | 4-NH₂ | H | H | piperidin-1-yl | 250 (d) |
| Ex. 12 (c) | CRL 41 243 | 4-NH₂ | H | H | 4-methylpiperazin-1-yl | 230 (d) |
| Ex. 13 (a) | CRL 41 246 | 4-NH₂ | H | H | NH-cyclopropyl | 150 (d) |
| Ex. 14 (a) | CRL 41 248 | 4-NH₂ | H | H | thiomorpholin-4-yl | 190–200 (d) |
| Ex. 15 (a) | CRL 41 255 | 3-NH₂ | H | H | NHCH(CH₃)₂ | 200 (d) |
| Ex. 16 (a) | CRL 41 260 | 3-NH₂ | H | H | N(CH₃)₂ | 210 (d) |
| Ex. 17 (a) | CRL 41 263 | 3-NH₂ | H | H | piperidin-1-yl | 200 (d) |

TABLE I-continued

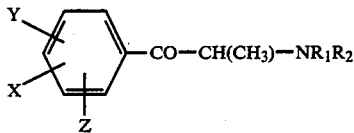

| PRODUCT | CODE NO. | X | Y | Z | $NR_1R_2$ | M.p. (°C.) |
|---|---|---|---|---|---|---|
| Ex. 18 (a) | CRL 41 268 | 3-$NH_2$ | H | H | 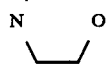 | 210 (d) |
| Ex. 19 (a) | CRL 41 278 | 3-$NH_2$ | H | H | $NHCH_2CH_2CH_3$ | 190 (d) |

Notes
(a) dihydrochloride
(b) monohydrochloride
(c) trihydrochloride
(d) with decomposition
(e) above 260° C.

The preferred compounds according to the invention include 1-(4-aminophenyl)-2-isopropylamino-, 1-(4-aminophenyl)-2-tert.-butylamino-, 1-(4-amino-3-chlorophenyl)-2-isopropylamino-, 1-(4-aminophenyl)-2-pyrrolidino-, 1-(4-aminophenyl)-2-ethylamino-, 1-(4-aminophenyl)-2-dimethylamino- and 1-(4-aminophenyl)-2-cyclopropylamino-propanones and addition salts thereof, and especially 1-(4-amino-3,5-dichlorophenyl)-2-isopropylamino- and 1-(4-aminophenyl)-2-morpholinopropanones and addition salts thereof.

The new 1-(aminophenyl)-2-aminopropanone derivatives can be prepared according to a method known per se by the application of conventional reaction mechanisms. According to the invention, two methods of synthesis, represented schematically by the following reactions, are recommended for the preparation of these derivatives:

Variant A:

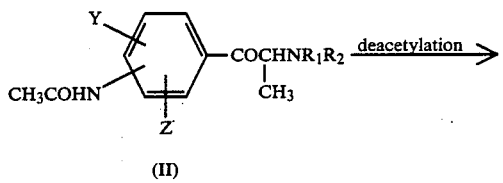

Variant B:

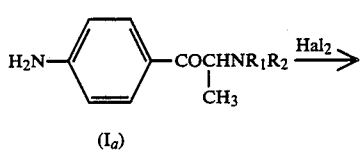

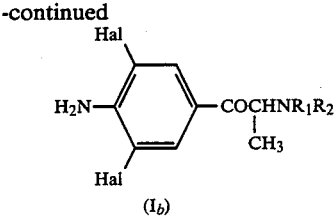

Variant A according to the invention consists in subjecting a 1-(acetylaminophenyl)-2-aminopropanone derivative of the formula II (in which Y, Z, $R_1$ and $R_2$ are defined as indicated above) to a deacetylation reaction with an aqueous solution of HCl, for at least 0.25 hour, at the reflux temperature of the reaction medium.

The deacetylation is advantageously carried out by reacting 1 mol of compound II with 0.7 liter to 2 liters of 4N HCl for 0.25 hour to 1 hour at the reflux temperature of the reaction medium.

Variant B relates to a particular method for the preparation of compounds of the formula I in which X=4-$NH_2$ and Y=Z=Hal (Hal denoting a halogen atom, especially F, Cl or Br and preferably Cl).

In variant B, a compound of the formula $I_a$ (in which $R_1$ and $R_2$ are defined as indicated above) is subjected to a halogenation reaction, in an aqueous medium, with a gaseous stream of $Hal_2$, for at least 0.25 hour. Advantageously, to carry out the method according to variant B, 2 mol of $Hal_2$ are reacted in water with 1 mol of 1-(aminophenyl)-2-aminopropanone of the formula $I_a$, at a temperature of between 8° C. and 15° C. (preferably 10° C.), for at least 0.25 hour (preferably for 0.25 hour to 1 hour).

Of course, variant A is the more convenient in the sense that it is applicable to the synthesis of all the compounds of the formula I according to the invention.

The new 1-(aminophenyl)-2-aminopropanone derivatives according to the invention are useful in therapy. They are all active on the CNS and all have antidepressant effects in particular. The results of neuropsychopharmacological tests show that the majority of these derivatives have stimulant or excitant effects. In addition to the common effects on the CNS (such as the antidepressant effects which appear with a greater or lesser intensity), some of these compounds also have valuable immunological and/or cardiovascular properties In particular, the products of Examples 3 (CRL 41 194), 6 (CRL 41 221), 10 (CRL 41 237) and 14 (CRL 41 248) possess immunostimulant or immunomodulating effects.

The most valuable products from the pharmaceutical point of view are:

(a) on account of their neuropsychopharmacolocical properties: the products of Examples 1 (CRL 41 153), 2 (CRL 41 178) and 4 (CRL 41 213);

(b) on account of their vasodiating properties the products of Examples 6 (CRL 41 221) 7 (CRL 41 222), 8 (CRL 41 225), 9 (CRL 41 233) and 13 (CRL 41 246); and (c) especially the product of Example 3 (CRL 41 194), which is a good vasodilator and possesses beneficial immunological properties, and the product of Example 10 (CRL 41 237), which is a good antidepressant and possesses immunostimulant effects.

According to the invention, a therapeutic composition is recommended which contains, in association with a physiologically acceptable excipient, at least one 1-(aminophenyl)-2-aminopropanone derivative, or one of its non-toxic addition salts, as the active principle.

Of course, in a composition of this type, the active principle is present in a pharmaceutically effective quantity.

Further advantages and characteristics of the invention will be understood more clearly on reading the following description of preparative examples on the one hand and results of pharmacological tests on the other; these data as a whole do not in any way imply a limitation but are given by way of illustration

PREPARATION I

Preparation of 1-(4-amino-3-chlorophenyl)-2-isopropylaminopropanone hydrochloride

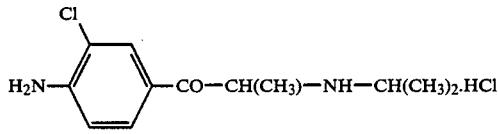

(Example 6; code no.: CRL 41 221)

(a) 1-(4-Acetylamino-3-chlorophenyl)-2-chloropropanone 45 g of 1-(4-acetylaminophenyl)-2-chloropropanone are suspended in 400 ml of chloroform. 0.2 mol of chlorine is bubbled in. The resulting reaction medium (which is a yellow solution) is evaporated to dryness and the evaporation residue is recrystallized from toluene to give 26 g (yield: 50%) of 1-(4-acetylamino-3-chlorophenyl)-2-chloropropanone. M.p. (inst.)=118° C.

(b) 1-(4-Acetylamino-3-chlorophenyl)-2-isopropylaminopropanone hydrochloride 26 g of 1-(4-acetylamino-3-chlorophenyl)-2-chloropropanone are dissolved in 150 ml of isopropylamine and the resulting reaction medium is then heated under reflux for 4 hours. The excess isopropylamine is evaporated off in vacuo, the remaining oily product is taken up in ethanol and the expected hydrochloride is precipitated with HCl gas to give 9.6 g (yield: 15%) of 1-(4-acetylamino-3-chlorophenyl)-2-isopropylaminopropanone hydrochloride. M.p. (inst.)=260° C.

(c) CRL 41 221

9.6 g of 1-(4-acetylamino-3-chlorophenyl)-2-isopropylaminopropanone hydrochloride are dissolved in 50 ml of 4N HCl and the solution is then heated under reflux for 0.5 hour. After evaporation in vacuo and recrystallization from ethanol, 7.6 g (yield: 13.7%) of CRL 41 221 are obtained. M.p. (inst.)=260° C.

PREPARATION II

Preparation of 1-(4-aminophenyl)-2-pyrrolidinopropanone dihydrochloride

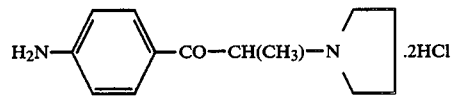

(Example 7; code no.: CRL 41 222)

22.6 g of 1-(4-acetylaminophenyl)-2-chloropropanone are dissolved in 50 ml of pyrrolidine and 20 ml of H$_2$O and the resulting mixture is heated under reflux for 2 hours. The unreacted excess pyrrolidine is evaporated off in vacuo and the oily evaporation residue is then taken up in 100 ml of 4N HCl. The mixture is heated under reflux for 0.5 hour and evaporated in vacuo and the residue is crystallized from ethanol to give 11.5 g (yield: 40%) of CRL 41 222. M.p. (inst.)=200° C.

PREPARATION III

Preparation of 1-(4-aminophenyl)-2-isopropylaminopropanone dihydrochloride

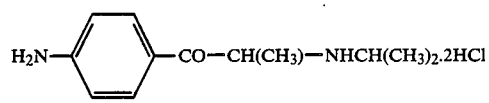

(Example 1; code no.: CRL 41 153)

10 g of 1-(4-acetylaminophenyl)-2-isopropylaminopropanone hydrochloride are dissolved in 100 ml of 4N HCl and the solution is heated under reflux for 0.5 hour. After evaporation in vacuo and recrystalization from a methanol/acetone mixture (1:1 v/v), 16.7 g (yield: 60%) of CRL 41 153 are obtained. M.p. (inst.)=210° C.

PREPARATION IV

Preparation of 1-(4-amino-3,5-dichlorophenyl)-2-isopropylaminopropanone hydrochloride

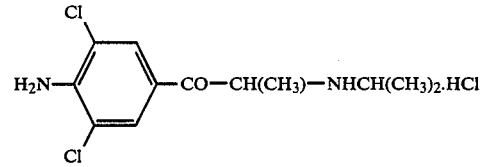

(Example 3; code no.: CRL 41 194)

0.2 mol of chlorine is bubbled into a solution of 28 g of 1-(4-aminophenyl)-2-isopropylaminopropanone dihydrochloride in 100 ml of H$_2$O, kept at about 10° C. After stirring for 2 hours, the mixture is evaporated to dryness in vacuo. The evaporation residue is taken up in acetic acid and crystallization gives 11 g (yield: 35%) of CRL 41 194. M.p. (inst.)>260° C.

PREPARATION V

Preparation of 1-(4-aminophenyl)-2-morpholinopropanone dihydrochloride

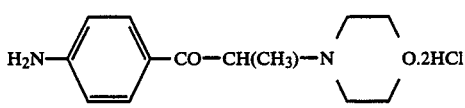

(Example 10; code no.: CRL 41 237)

A solution of 19 g (0.0608 mol) of 1-(4-acetylaminophenyl)-2-morpholinopropanone hydrochloride in 100 ml of 4N HCl is heated under reflux for 1 hour. It is evaporated to dryness under reduced pressure and the evaporation residue is taken up with benzene, which is distilled azeotropically by means of a Dean-Stark apparatus. The expected product crystallizes. 11.2 g (yield: 60%) of CRL 41 237 are collected by filtration. M.p. (inst.)=210° C. (with decomposition).

PREPARATION VI

Preparation of 1-(3-aminophenyl)-2-piperidinopropanone dihydrochloride

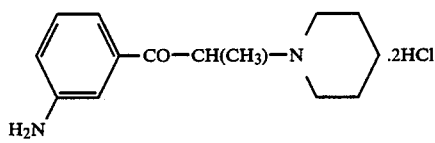

(Example 17; code no.: CRL 41 263)

A solution of 9.9 g (0.0318 mol) of 1-(3-acetylaminophenyl)-2-piperidinopropanone hydrochloride in 50 ml of 4N hydrochloric acid is heated under reflux for 1 hour. The reaction medium is evaporated to dryness under reduced pressure and the residue is taken up with benzene, which is distilled azeotropically by means of a Dean-Stark apparatus. Filtration of the precipitate formed gives 9.8 g (yield: about 100%) of CRL 41 263. M.P. (inst.)=200° C. (with decomposition).

PREPARATION VII

Preparation of 1-4-aminophenyl)-2-methylaminopropanone dihydrochloride

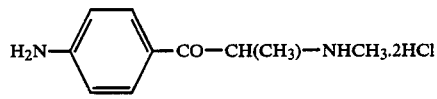

(Example 5; code no.: CRL 41 218)

A solution of 5.5 g (0.021 mol) of 1-(4-acetylaminophenyl)-2-methylaminopropanone hydrochloride in 35 ml of 4N HCl is heated under reflux for 0.25 hour. The reaction medium is evaporated to dryness and the evaporation residue is taken up with benzene, which is distilled azeotropically by means of a Dean-Stark apparatus. The precipitate formed is purified by washing in hot methanol. This gives 3.8 g (yield 72%) of CRL 41 218. M.p. (inst.)=220° C. (with decomposition).

Some of the results of the tests which were undertaken with the compounds according to the invention have been summarized below.

A. TESTS RELATING TO CRL 41 153 (PRODUCT OF EXAMPLE 1)

In the neuropsychopharmacological study which follows, a solution of CRL 41 153 in distilled water (pH 1.5) was administered intraperitoneally in a volume of 20 ml/kg to male mice and 5 ml/kg to male rats.

I. TOXICITY

In male mice, the $LD_0$ (maximum non-lethal dose) by intraperitoneal administration is greater than 64 mg/kg and the $LD_{60}$ is of the order of about 128 mg/kg.

II. OVERALL BEHAVIOR AND REACTIVITIES

Groups of three animals are observed before and then 0.25 hour, 0.50 hour, 1 hour, 2 hours, 3 hours and 24 hours after the administration of CRL 41 153. The following observations are made:
(1°) in mice
  at a dose of 0.5 mg/kg:
    no particular symptoms;
  at a dose of 2 mg/kg:
    excitation of low intensity 0.5 hour after administration,
    stereotypies for 1 hour, and
    an increase in the fear reaction (for 1 hour) and in the reactivity to touch (2 to 3 hours after administration);
  at a dose of 8 mg/kg:
    excitation for 3 hours, and
    an increase in the fear reaction (for 3 hours) and in the reactivity to touch (for 24 hours); and
  at a dose of 32 mg/kg:
    excitation and stereotypies for 3 hours,
    an increase in the fear reaction (for 2 hours) and in the reactivity to touch (for 24 hours),
    slight hyperthermia (+1.1° C.) 0.5 hour after administration, and
    moderate mydriasis;
(2°) in rats
  at a dose of 0.25 mg/kg:
    no particular symptoms;
  at a dose of 1 mg/kg:
    mydriasis for 1 hour, reaching its maximum value 1 hour after administration;
  at a dose of 4 mg/kg:
    excitation 0.5 hour after administration and stereotypies for 2 hours,
    hyperthermia for 3 hours, at a maximum 0.5 hour after administration (+1.9° C.), and
    mydriasis for 2 hours, reaching its maximum value 0.5 hour after administration; and
  at a dose of 16 mg/kg:
    excitation 0.5 hour after administration,
    stereotypies for 3 hours,
    an increase in the fear reaction for 3 hours, and
    mydriasis for 3 hours, at a maximum 0.5 hour after administration.

III. INTERACTION WITH APOMORPHINE (1°) In mice
Groups of 6 mice receive CRL 41 153 0.5 hour before the subcutaneous injection of 1 or 16 mg/kg of apomorphine. It is observed that, at doses of 2 mg/kg, 8 mg/kg and 32 mg/kg, CRL 41 153 (which is hyperthermic at the said doses) opposes the hypothermia induced by apomorphine, without modifying the righting behavior and stereotypy behavior.

(2°) In rats

CRL 41 153 is administered to groups of 6 rats 0.5 hour before the subcutaneous injection of 0.5 mg/kg of apomorphine. It is observed that, as from a dose of 0.5 mg/kg, CRL 41 153 potentiates the stereotypies induced by apomorphine.

IV. INTERACTION WITH AMPHETAMINE

Amphetamine (2 mg/kg) is injected intraperitoneally into groups of 6 rats 30 minutes after the administration of CRL 41 153. It is found that, at doses of 1 mg/kg. 4 mg/kg and 16 mg/kg, CRL 41 153 potentiates the intensity and duration of the stereotypies induced by amphetamine.

V. INTERACTION WITH RESERPINE

Four hours after the intraperitoneal injection of 2.5 mg/kg of reserpine, groups of 6 mice receive CRL 41 153.

It is noted that, as from a dose of 0.5 mg/kg, CRL 41 153 strongly opposes the hypothermia and ptosis induced by reserpine.

VI. INTERACTION WITH OXOTREMORINE

CRL 41 153 is administered to groups of 6 mice 0.5 hour before the intraperitoneal injection of 0.5 mg/kg of oxotremorine.

(1°) Action on the temperature

It is found that, at doses of 2 mg/kg, 8 mg/kg and 32 mg/kg, CRL 41 153 opposes the hypothermic action of oxotremorine.

(2°) Action on the trembling

It is found that, at doses of 8 mg/kg and 32 mg/kg, CRL 41 153 partially antagonizes the trembling induced by oxotremorine.

(3°) Action on the peripheral cholinergic symptoms

It is observed that CRL 41 153 possesses a moderate α-adrenergic stimulant effect.

VII. ACTION ON THE FOUR PLATE TEST, TRACTION AND ELECTRIC SHOCK

The test is performed on groups of 10 mice 30 minutes after the administration of CRL 41 153.

It is found that, at high doses, CRL 41 153 antagonizes the convulsant effects of electric shock.

VIII. ACTION ON THE SPONTANEOUS MOTILITY 0.5 hour after they have received CRL 41 153, the mice (6 per dose, 12 control animals) are placed in an actimeter, where their motility is recorded for 30 minutes.

It is observed that CRL 41 153 increases the spontaneous motor activity of mice.

IX. ACTION ON THE INTERGROUP AGGRESSIVENESS

After they have stayed for 3 weeks in the two halves of a cage divided by an opaque partition, groups of 3 mice receive CRL 41 153. Half an hour later, the two groups from the same cage are brought together by removal of the partition, and the number of fights which occur in 10 minutes is noted.

It is found that, at a dose of 8 mg/kg, CRL 41 153 reduces the number of fights.

X. ACTION TOWARDS SOME FORMS OF BEHAVIOR PERTURBED BY VARIOUS AGENTS (1°) Motility reduced by habituation to the enclosure After they have stayed In the actimeters for 18 hours, (he mice (6 per dose, 12 control animals) receive CRL 41 153. They are immediately returned to their respective enclosures and, half an hour later, their motility is recorded for 30 minutes.

It is observed that CRL 41 153 causes a distinct resumption in the motor activity of mice accustomed to their enclosure.

(2°) Motility reduced by hypoxic aggression

Half an hour after they have received CRL 41 153, the mice (10 per dose, 20 control animals) are subjected to acute hypobaric anoxia [pressure reduction of 600 mm Hg (i.e. about $8 \times 10^4$ Pa) in 90 seconds; release of vacuum in 45 seconds] and are then placed in an actimeter, where their motility is recorded for 10 minutes.

It is observed that, as from a dose of 0.5 mg/kg, CRL 41 153 causes a distinct improvement in the motor recovery of mice whose motility has been depressed following a brief period in a reduced-pressure enclosure.

(3°) Asphyxiant anoxia

Groups of 10 mice receive CRL 41 153 half an hour before the intraperitoneal administration of 32 mg/kg of gallamine triiodoethylate (reference curarizing agent).

It is observed that, at a dose of 32 mg/kg, CRL 41 153 reduces the time taken for convulsions to occur and does not change the time taken for death to occur following asphyxiant anoxia caused by a curarizing agent.

XI. INTERACTION WITH BARBITAL

Half an hour after the administration of CRL 41 153, groups of 10 mice receive an intraperitoneal injection of barbital (220 mg/kg).

It is found that, at doses of 0.5 to 32 mg/kg, CRL 41 153 increases the time taken to fall asleep and reduces the duration of the sleep induced by barbital (total antagonism is obtained at doses of 8 mg/kg and 32 mg/kg).

XII. ACTION ON THE "BEHAVIORAL DESPAIR"

Half an hour after they have received CRL 41 153, groups of 6 mice are placed in a beaker filled with water to a height of 6 cm. The total period of immobility between the 2nd and 6th minutes following immersion is noted.

It is observed that, at doses greater than or equal to 0.5 mg/kg, CRL 41 153 reduces the period of immobility of mice which have been forcibly immersed.

XII. CONCLUSIONS

The above neuropsychopharmacological tests as a whole show that CRL 41 153 has antidepressant effects: antagonism of the hypothermia induced by apomorphine, reserpine or oxotremorine, and reduction in the period of immobility due to "despair";

stimulant effects: excitation in mice and rats, presence of stereotype movements in mice and rats, potentiation of the stereotypies induced by apomorphine and amphetamine, increase in the motor activity, improvement in the motor recovery of mice whose motility has been depressed following a brief period in a reduced-pressure enclosure, and distinct improvement in the motor activity of mice accustomed to their enclosure;

peripheral α-adrenergic stimulant effects: mydriasis (with neither piloerection nor salivation) and antagonism of the ptosis induced by reserpine; and anticonvulsant effects: at a high dose.

It follows that CRL 41 153 behaves as an antidepressant for the CNS. The antidepressant effect is associated with a distinct stimulant component

XIV. COMPLEMENTARY TESTS (1°) Oral administration

The tests undertaken by gastric administration show that CRL 41 153 is a very active substance according to the tests used:

hypermotility;

reduction in the sleep induced by barbital, and antagonism of the hypothermia induced by apomorphine.

In general, it is observed that, by gastric administration, the antidepressant effects and the stimulant and/or arousing effects appear as from a dose of 4 mg/kg. CRL 41 153 therefore has the same types of action on gastric administration as after intraperitoneal administration; the stimulant-type and/or arousing-type effects and the antidepressant-type effects develop at comparable doses.

(2°) Cardiovascular study

It is found that, in anesthetized dogs, CRL 41 153 increases the blood flow through the femoral artery and the blood flow through the vertebral artery at doses of 2.5 to 5 mg/kg, administered orally. The increase in the femoral and vertebral flows is suppressed by propanolol. It is also observed that CRL 41 153 does not modify the effects of isoprenaline on the blood pressure and that it has a moderate α-adrenergic stimulant effect. The reflex bradycardia caused by hypertension is converted to tachycardia (the origin of this effect would be of an atropinic or ganglioplegic nature).

(3°) Difference from amphetamine

CRL 41 153 differs from amphetamine in the mechanism of its effects which cause stereotypies and its action on the nigrostriatal dopaminergic system (this action being explored by the interaction with alpha-methyltyrosine, which totally inhibits the stereotypies induced by amphetamine but only reduces them in the case of CRL 41 153).

B. TESTS RELATING TO CRL 41 178 (PRODUCT OF EXAMPLE 2)

The neuropsychopharmacological study of CRL 41 178, undertaken according to the procedures described above for CRL 41 153, shows that the said CRL 41 178, administered intraperitoneally, has distinct stimulant effects: excitation and hyperreactivity in mice and rats, presence of stereotype movements and potentiation of the effects of apomorphine and amphetamine in rats, antagonism of the sleep induced by barbital, increase in the motor activity, resumption in the activity of mice accustomed to their enclosure, and improvement in the motor recovery of mice whose activity has been depressed following hypobaric hypoxia; more modest antidepressant effects: antagonism of the hypothermia induced by reserpine, oxotremorine or apomorphine, and reduction in the period of immobility due to "despair";

moderate α-adrenergic stimulant effects: mydriasis (with neither piloerection nor salivation) and slight antagonism of the ptosis induced by reserpine; and anticonvulsant effects: at high doses, antagonism of the convulsant effects of electric shock.

In all these tests, CRL 41 178 behaves as a stimulant as from the weakest doses. The stimulant effects are associated with an antidepressant component.

On gastric administration, CRL 41 178 has the same types of action as after intraperitoneal administration. It should be pointed out that the antidepressant effects are apparently developed better by oral administration than by intraperitoneal administration.

Difference from amphetamine

The stereotypies induced by amphetamine, which are totally inhibited after blocking of the catecholamine synthesis by α-methyltyrosine, seem to depend essentially on a pool of newly synthesized catecholamines (probably dopamine). This pool seems to be at least partially involved in the mechanism which underlies the stereotypies induced by CRL 41 178.

CRL 41 178 is similar to amphetamine, especially in the presence of stereotype movements and the existence of a particular toxicity to grouped mice, but differs from amphetamine in the mechanism of the effects which cause stereotypies.

C. TESTS RELATING TO CRL 41 194 (PRODUCT OF EXAMPLE 3) - NEUROPSYCHOPHARMACOLOGICAL TESTS

The neuropsychopharmacological tests were undertaken according to the procedures described above for CRL 41 153. In these tests, unless stated otherwise, CRL 41 194 was administered intraperitoneally, in solution in distilled water (pH 4.5), in a volume of 20 ml/kg to male mice and 5 ml/kg to male rats.

I. TOXICITY

In male mice, the $LD_0$ by intraperitoneal administration is greater than 32 mg/kg and the $LD_{50}$ is equal to 86 mg/kg.

II. OVERALL BEHAVIOR AND REACTIVITIES

The following observations are made:

(1°) in mice at doses of 0.25 mg/kg and 1 mg/kg:
weak excitation 24 hours after administration;

at a dose of 4 mg/kg:
weak excitation and an increase in the reactivity to touch about 24 hours after administration; and at a dose of 16 mg/kg:
weak excitation 24 hours after administration,
an increase in the reactivity to touch for 24 hours,
dyspnea for 3 hours,
mydriasis for 2 hours (at a maximum 1 hour after administration), and
dilation of the caudal veins for 2 hours;

(2°) in rats at a dose of 0.125 mg/kg:
mydriasis for 2 hours (at a maximum 0.5 hour after administration);

at a dose of 0.5 mg/kg:
dyspnea for 0.5 hour;

at a dose of 2 mg/kg:
mydriasis at a maximum 0.5 hour after administration, and
dyspnea for 2 hours; and at a dose of 8 mg/kg:

piloerection for 1 hour,
mydriasis for 2 hours (at a maximum 0.5 hour after administration), and
dyspnea for 2 hours.

III. INTERACTION WITH APOMORPHINE

It is found that, as from a dose of 2 mg/kg, administered gastrically, CRL 41 194 opposes the hypothermia induced in mice by the subcutaneous injection of 16 mg/kg of apomorphine, without modifying the righting behavior and the stereotypies.

IV. ACTION ON THE SPONTANEOUS MOTILITY

At the strongest dose administered gastrically (32 mg/kg), CRL 41 194 slightly reduces the spontaneous motor activity of mice.

V. INTERACTION WITH BARBITAL

At the strongest dose administered gastrically (32 mg/kg), CRL 41 194 reduces the duration of the sleep induced by barbital in mice.

VI. INVESTIGATION OF STEREOTYPE MOVEMENTS

Immediately after the intraperitoneal administration of CRL 41 194 or amphetamine, groups of 6 rats are placed in Plexiglass boxes (20×10×10 cm). The stereotype movements are graded from 0 to 3 every 10 minutes until they wear off.

At the strongest dose used (16 mg/kg), CRL 41 194 causes the appearance of stereotype movements. The intensity of the effect obtained with 16 mg/kg is slightly lower than that obtained with 2 mg/kg of amphetamine.

VII. INVESTIGATION OF A PARTICULAR TOXICITY IN GROUPED MICE

Immediately after the intraperitgneal administration of CRL 41 194, groups of 10 mice are placed in Plexiglass boxes (20×10×10 cm). The number of dead animals is noted after 1 hour, 2 hours, 3 hours, 4 hours and 24 hours. The toxicity of CRL 41 194 is determined under the same conditions on groups of isolated mice, i.e. mice placed in boxes with one mouse per box.

The $LD_{50}$ of CRL 41 194 is equal to:
86 mg/kg in isolated mice,
27 mg/kg in grouped mice.

The ratio $LD_{50}$ for isolated mice/$LD_{50}$ for grouped mice is equal to 3.19 (statistically significant).

CRL 41 194 is therefore more toxic to grouped mice than to isolated mice. By way of comparison, the ratio $LD_{50}$ for isolated mice/$LD_{50}$ for grouped mice, under the same conditions, is:
about 8 for amphetamine,
about 4 for nomifensin and benzphetamine,
about 6 for methylphenidate.

VIII. CONCLUSION

In these tests, CRL 41 194, administered intraperitoneally or gastrically, is an antidepressant. For intraperitoneal administration, it is found that the antidepressant effects appear at the same time as stereotype movements (of moderate intensity).

CARDIOVASCULAR STUDY

Two dogs (average weight: 14.1 kg), anesthetized with nembutal, receive CRL 41 194 by intraduodenal administration at successive doses of 0.1 mg/kg, 0.5 mg/kg, 1 mg/kg, 2.5 mg/kg, 5 mg/kg and 10 mg/kg (in solution in physiological solvent).

The blood pressure, the heart rate, the blood flow through the femoral artery, the blood flow through the vertebral artery and the rectal temperature are measured. The coloration of the skin and the coloration of the bile, collected by catheterization of the bile duct after ligature of the cystic duct, are observed.

It is found that CRL 41 194 increases the vertebral flow as from a dose of 0.1 mg/kg, administered intraduodenally.

At 0.5 mg/kg, the femoral flow increases at the same time as the heart rate. A drop in the diastolic blood pressure is observed at 5 mg/kg, together with an increase in the differential blood pressure as from the smallest doses. Both dogs received respiratory stimulation and the rectal temperature and skin temperature rose.

The effects of isoprenaline, tested after an accumulated dose of 19.1 mg/kg, administered intraduodenally, are not modified as regards the heart rate and are reduced as regards the blood pressure.

With 10 μg/kg of isoprenaline, the diastolic blood pressure changes from 126 mm Hg (i.e. about $1.67 \times 10^4$ pa) to 64 mm Hg (i.e. about $8.5 \times 10^3$ Pa) after CRL 41 194, instead of changing from 154 mm Hg (i.e. about $2.05 \times 10^4$ Pa) to 38 mm Hg (i.e. about $5.06 \times 10^3$ Pa) in the control animals, and the heart rate changes from 2.1 beats/minute to 262 beats/minute after CRL 41 194, instead of changing from 152 beats/minute to 260 beats/minute in the control animals.

The hypertension induced by norepinephrine is slightly reduced by CRL 41 194. With 2 μg/kg of norepinephrine, the systolic blood pressure changes from 208 mm Hg (i.e. about $2.77 \times 10^4$ Pa) to 266 mm Hg (i.e. about $3.54 \times 10^4$ Pa) instead of changing from 178 mm Hg (i.e. about $2.37 \times 10^4$ Pa) to 312 mm Hg (i.e. about $4.15 \times 10^4$ Pa) in the control animals.

IMMUNOLOGICAL STUDY

CRL 41 194 is active on the cellular and humoral immunity according to the so-called test for cells forming lysis areas described by A. J CUNNINGHAM et al. ("Further improvements in the plague technique for detecting single antibody forming cells"), immunology 14, pages 599–601 (1968), and according to measurement of the intensity of the decayed hypersensitivity to the red blood corpuscles of sheep, described by T. E. MILLER et al. ("Immunopotentiation with BCG II modulation of the response to sheep blood cells"), Journal of the National Cancer Institute 51 (No. 5), pages 1669–1676 (1973). The corresponding tests show that CRL 41 194 behaves as an immunomodulating agent.

CLINICAL STUDY

In human clinical trials, CRL 41 194 was shown to be very active as a vasodilator. In the treatment of diseases associated with the blood circulation through the vessels.

Furthermore, it also gave excellent results on man in the treatment of depressions at a dose of 3×5 mg per day, especially in the form of tablets or gelatine capsules each containing 5 mg of CRL 41 194, taken three times a day.

D TESTS RELATING TO CRL 41 213 (PRODUCT OF EXAMPLE 4)

The neuropsychopharmacological study was undertaken according to the procedures described above for CRL 41 153, CRL 41 213 being adminstered intraperitoneally, in solution in distilled water, in a volume of 20 ml/kg to male mice and a volume of 5 ml/kg to male rats, and the pH of the injected solution varying with the concentration of CRL 41 213 according to the data given in Table II below.

Variation in the pH of solutions of certain compounds according to the invention in distilled water.

TABLE II

Variation in the pH of solutions of certain compounds according to the invention in distilled water.

| PRODUCT | CONCENTRATION (g/liter) | pH |
|---|---|---|
| Ex. 4 (CRL 41 213) | 50 | 1.0 |
|  | 25 | 1.5 |
|  | 3.2 | 2.0 |
|  | 1.6 | 2.5 |
|  | 0.8 | 3.0 |
|  | 0.4 | 3.5 |
|  | 0.2 | 4.0 |
|  | $\leq 0.1$ | 5.0 |
| Ex. 5 (CRL 41 218) | 50 | 4.0 |
|  | 13 | 4.5 |
|  | 6 | 5.0 |
|  | $\leq 3$ | 5.5 |
| Ex. 6 (CRL 41 221) | 50 | 4.0 |
|  | 13 | 4.5 |
|  | 6 | 5.0 |
|  | $\leq 3$ | 5.5 |
| Ex. 7 (CRL 41 222) | 12.8 | 1.5 |
|  | 6.4 | 2.0 |
|  | 3.2 | 2.5 |
|  | 1.6 | 3.0 |
|  | 0.8 | 3.5 |
|  | 0.4 | 4.0 |
|  | 0.2 | 4.5 |
|  | 0.1 | 5 |
|  | $\leq 0.05$ | 5.5 |
| Ex. 8 (CRL 41 225) | 50 | 1.5 |
|  | 13 | 2.0 |
|  | 3 | 2.5 |
|  | 2 | 3.0 |
|  | 0.8 | 3.5 |
|  | 0.4 | 4.0 |
|  | 0.2 | 4.5 |
|  | 0.1 | 5.0 |
|  | $\leq 0.05$ | 5.5 |
| Ex. 9 (CRL 41 233) | 50 | 1.0 |
|  | 12.8 | 1.5 |
|  | 6.4 | 2.0 |
|  | 3.2 | 2.5 |
|  | 1.6 | 3.0 |
|  | 0.8 | 3.5 |
|  | 0.4 | 4.0 |
|  | 0.2 | 4.5 |
|  | 0.1 | 5.0 |
|  | $\leq 0.05$ | 5.5 |
| Ex. 10 (CRL 41 237) | 50 | 1.0 |
|  | 25 | 1.5 |
|  | 6.4 | 2.0 |
|  | 3.2 | 2.5 |
|  | 1.6 | 3.0 |
|  | 0.8 | 3.5 |
|  | 0.4 | 4.0 |
|  | 0.2 | 4.5 |
|  | 0.1 | 5.0 |
|  | $\leq 0.05$ | 5.5 |
| Ex. 11 (CRL 41 241) | 50 | 1.0 |
|  | 26 | 1.5 |
|  | 6 | 2.0 |
|  | 3 | 2.5 |
|  | 2 | 3.0 |
|  | 1 | 3.5 |
|  | 0.5 | 4.5 |
|  | 0.3 | 5.0 |
|  | $\leq 0.05$ | 5.5 |
| Ex. 12 (CRL 41 243) | 50 | 1.0 |
|  | 25 | 1.5 |
|  | 6.4 | 2.0 |
|  | 3.2 | 2.5 |
|  | 0.8 | 3.5 |
|  | 0.4 | 4.0 |
|  | 0.2 | 4.5 |
|  | 0.1 | 5.0 |
|  | $\leq 0.05$ | 5.5 |
| Ex. 13 (CRL 41 246) | 12.8 | 2.5 |
|  | 6.4 | 3.0 |
|  | 1.6 | 3.5 |
|  | 0.8 | 4.0 |
|  | 0.4 | 4.5 |
|  | 0.1 | 5.0 |
|  | $\leq 0.05$ | 5.5 |
| Ex. 14 (CRL 41 248) | 50 | 1.5 |
|  | 6.4 | 2.0 |
|  | 3.2 | 2.5 |
|  | 1.2–0.8 | 3.0 |
|  | 0.4 | 3.5 |
|  | 0.2 | 4.0 |
|  | 0.1 | 4.5 |
|  | 0.05 | 5.0 |
|  | $\leq 0.025$ | 5.5 |

I. TOXICITY

When administered intraperitoneally to male mice, CRL 41 213 has an $LD_0$ greater than or equal to 128 mg/kg and an $LD_{100}$ less than or equal to 256 mg/kg.

II. OVERALL BEHAVIOR AND REACTIVITIES (1°) In mice
at a dose of 1 mg/kg:
  moderate sedation 0.5 hour after administration;
at a dose of 4 mg/kg:
  moderate excitation 0.5 hour after administration, and
  piloerection for 0.25 hour;
at a dose of 16 mg/kg:
  excitation for more than 3 hours with the presence of stereotypies for about 2 hours as from the 1st hour following administration,
  an increase in the fear reaction, the reactivity to touch and the aggressiveness for more than 3 hour, and
  salivation, lacrimation and exophthalmos for 1 hour, and
  polypnea; and
at a dose of 64 mg/kg
  clonic convulsions for 0.5 hour,
  excitation for more than 3 hours with the presence of stereotypies,
  an increase in the fear reaction and the reactivity to touch from 2 hours to more than 3 hours,
  mydriasis for more than 3 hours, and
  polypnea;
(2°) in rats
at a dose of 0.5 mg/kg:
  mydriasis for 1 hour;
at a dose of 2 mg/kg
  excitation with the presence of stereotypies, and
  an increase in the fear reaction and in the reactivity to touch and noise for 2 hours;
at a dose of 8 mg/kg:
  excitation with the presence of stereotypies, an increase in the fear reaction and in the reactivity to touch and noise for 3 hours, and
mydriasis for more than 3 hours; and at a dose of 32 mg/kg:
excitation with the presence of very intense stereotypies,
an increase in the fear reaction and in the reactivity to touch and noise for 3 hours,
exophthalmos from 0.5 hour to 3 hours,
mydriasis for 3 hours, and
polypnea.

INVESTIGATION OF STEREOTYPE MOVEMENTS

Groups of 6 rats receive an intraperitoneal injection of CRL 41 213, distilled water or amphetamine immediately before being placed in small cages, where their stereotype behavior is graded every 10 minutes until the effect wears off.

As from a dose of 2 mg/kg, CRL 41 213 causes the appearance of stereotype movements in rats, the intensity of which is substantially comparable to that obtained with 2 mg/kg of amphetamine. Increasing the doses leads to an increase in the intensity and duration of these stereotypies.

IV. INTERACTION WITH APOMORPHINE (1°) In mice
15 It is observed that, at doses of 1 mg/kg, 4 mg/kg, 16 mg/kg and 64 mg/kg, CRL 41 213 strongly opposes the hypothermia induced by apomorphine in mice. At the strongest dose studied (64 mg/kg), CRL 41 213 moderately reduces the righting behavior without modifying the stereotypies induced by apomorphine.

(2°) In rats
It is found that, as from a dose of 2 mg/kg, CRL 41 213 causes an increase in the index of the stereotypes induced by apomorphine. This increase is large in terms of intensity and duration at doses of 8 mg/kg and 32 mg/kg of CRL 41 213.

V. INTERACTION WITH AMPHETAMINE

It is found that, as from a dose of 2 mg/kg, CRL 41 213 potentiates the stereotypies induced by amphetamine. The intensity and duration of the potentiation increase with the dose.

VI. INTERACTION WITH RESERPINE

It is observed that, at doses of 1 mg/kg and 4 mg/kg, CRL 41 213 opposes the hypothermic action of reserpine as well as the ptosis induced by reserpine, and that, at a weaker dose (0.25 mg/kg), no effect is detected.

VII. INTERACTION WITH OXOTREMORINE (1°) Action on the temperature
As from a dose of 4 mg/kg, CRL 41 213 opposes the hypothermic action of oxotremorine. At the weakest dose studied (1 mg/kg), this effect is scarcely detectable.

(2°) Action on the trembling
At the strongest doses (16 and 64 mg/kg), CRL 41 213 reduces the intensity of the trembling due to oxotremorine.

(3°) Action on the peripheral cholinergic symptoms
CRL 41 213 does not change the signs of peripheral cholinergic stimulation produced by oxotremorine.

VIII. ACTION ON THE FOUR PLATE TEST, TRACTION AND ELECTRIC SHOCK

At doses of 1 mg/kg, 4 mg/kg and 16 mg/kg, CRL 41 213 causes an increase in the number of punished passes. This increase is not present at the strongest dose used (64 mg/kg). At a strong dose, CRL 41 213 causes motor incapacity (64 mg/kg) and opposes the convulsant effects of electric shock 116 to 64 mg/kg). At the strongest dose used (64 mg/kg), the presence of clonic convulsions is liable to constitute a perturbation in the number of punished passes, the traction test and the convulsions induced by electric shock.

IX. ACTION ON THE SPONTANEOUS MOTILITY

At doses of 1 mg/kg, 4 mg/kg and 16 mg/kg, CRL 41 213 causes a substantial increase in the spontaneous motor activity of mice. At the strongest dose studied (64 mg/kg), CRL 41 213 causes clonic convulsions and stereotypies, which can interfere with the spontaneous motor activity of mice.

X. ACTION ON THE INTERGROUP AGGRESSIVENESS

It is observed that CRL 41 213 does not modify the intergroup aggressiveness of mice.

XI. ACTION TOWARDS SOME FORMS OF BEHAVIOR PERTURBED BY VARIOUS AGENTS (1°) Motility reduced by habituation to the enclosure
It is observed that, at doses of 4 mg/kg, 16 mg/kg and 64 mg/kg, CRL 41 213 causes a resumption in the motor activity of mice accustomed to their enclosure.

(2°) Motility reduced by hypoxic aggression
As from 1 mg/kg, CRL 41 213 causes a distinct improvement in the motor recovery of mice whose activity has been depressed following a brief period in a reduced-pressure enclosure.

(3°) Asphyxiant anoxia
It is found that CRL 41 213 does not modify (he time taken for convulsions to occur and that, at a dose of 64 mg/kg, it moderately increases the time taken for death to occur following asphyxiant anoxia caused by the reference curarizing agent gallamine triiodoethylate.

XII. INTERACTION WITH BARBITAL

It is observed that, as from a dose of 0.5 mg/kg. CRL 41 213 reduces the duration of the sleep induced by barbital. Total antagonism is obtained for doses equal to or greater than 4 mg/kg.

XIII. ACTION ON THE "BEHAVIORAL DESPAIR

It is found that, as from a dose of 0.5 mg/kg, CRL 41 213 distinctly reduces the period of immobility due to "despair". Total antagonism is obtained at doses of 4 mg/kg, 16 mg/kg and 64 mg/kg of CRL 41 213.

XIV. CONCLUSION

With regard to the results given above, the neuropsychopharmacological profile of CRL 41 213 shows stimulant effects:
excitation with hyperreactivity in mice and rats,
hyperactivity (increase in the motor activity, resumption in the motor activity of mice accustomed to their enclosure, improvement in the motor recovery of mice which have undergone hypoxic aggression, and increase in the number of punished passes in the 4 plate test),
antagonism of the sleep induced by barbital, and
presence of stereotype movements in mice and rats and potentiation of the stereotypies induced by amphetamine and apomorphine;
antidepressant effects:
antagonism of the hypothermia induced by apomorphine, reserpine and oxotremorine, and
reduction in the immobility due to "despair"; and
effects reflecting peripheral α-adrenergic stimulation:
antagonism of the ptosis induced by reserpine,
antagonism of the trembling caused by oxotremorinea,
mydriasis, and
presence of salivation, lacrimation and exophthalmos Furthermore, at high but non-toxic doses, CRL 41 213 causes the appearance of clonic convulsions but opposes the convulsant effects of electric shock. p In summary, according to all the tests mentioned above, CRL 41 213 behaves as a substance possessing antidepressant, stimulant and arousing properties. These properties are apparent at relatively weak doses.

E. TESTS RELATING TO CRL 41 218 (PRODUCT OF EXAMPLE 5)

The neuropsychopharmacological tests undertaken according to the procedures described above for CRL 41 153 show that CRL 41 218 has
antidepressant effects:
antagonism of the hypothermia induced by apomorphine, reserpine and oxotremorine, and
a reduction in the period of immobility due to "despair";
stimulant effects:
excitation in mice and rats with the presence of stereotype movements,
potentiation of the stereotypies induced by apomorphine and amphetamine,
distinct antagonism of the sleep induced by barbital, and
hyperactivity (increase in the motor activity, improvement in the motor recovery of mice whose motility has been depressed following a brief period in a reduced-pressure enclosure, and resumption in the motor activity of mice accustomed to their enclosure);
α-adrenergic stimulant effects:
mydriasis,
salivation, and
antagonism of the ptosis induced by reserpine; and
anticonvulsant effects:
antagonism, at strong doses, of the convulsant effects of electric shock.

F. TESTS RELATING TO CRL 41 221 (PRODUCT OF EXAMPLE 6)

I. Cardiovascular Study 4 dogs (average weight: 14 kg), anesthetized with nembutal, receive CRL 41 221 by intraduodenal administration at successive doses of 0.1 mg/kg, 0.5 mg/kg, 1 mg/kg, 2.5 mg/kg, 5 mg/kg and 10 mg/kg. The blood pressure, the heart rate, the blood flow through the femoral artery, the blood flow through the vertebral artery and the rectal temperature are measured. The coloration of the skin is observed.

It is found that CRL 41 221 bas a tachycardiac effect as from 2.5 mg/kg, that the femoral flow increases substantially as from this same dose and that the vertebral flow increases at a dose of 0.5 mg/kg. A reduction in the diastolic blood pressure is observed at 5 mg/kg and hypotension appears at 10 mg/kg.

It is observed that the rectal temperature and skin temperature rise gradually and that the respiration is stimulated.

It is noted that the effects of isoprenaline, tested after an accumulated dose of 19.1 mg/kg of CRL 41 221, are not modified as regards the diastolic blood pressure and that they are slightly reduced as regards the heart rate.

With 3 μg/kg of isoprenaline, the heart rate changes from 212 beats/minute to 262 beats/minute after CRL 41 221, instead of from 181 beats/minute to 272 beats/minute in the control animals.

The hypertension induced by norepinephrine is slightly reduced. With 2 μg/kg of norepinephrine, the systolic blood pressure changes from 158 mm Hg (i.e. about $2.10 \times 10^4$ pa) to 266 mm Hg (i.e. about $3.01 \times 10^4$ pa) instead of from 183 mm Hg (i.e. about $2.44 \times 10^4$ pa) to 302 mm Hg (i.e. about $4.02 \times 10^4$ Pa) in the control animals.

The injection of atenolol into 2 dogs reduces the effects of CRL 41 221 and the injection of propanolol does not increase the $\beta^-$ effects.

CRL 41 221 is consequently a vasodilator.

Neuropsychopharmacological Study

The tests undertaken according to the procedures described above for CRL 41 153 show that CRL 41 221 has
antidepressant effects:
antagonism of the hypothermia caused by reserpine, oxotremorine and apomorphine, and
a reduction in the period of immobility of mice which have been forcibly immersed (this may be related to the stimulant component); and
stimulant effects:
excitation with hyperreactivity in mice and rats,
an increase in the spontaneous motor activity of mice, with resumption in the motor activity of mice accustomed to their enclosure, and improvement in the motor recovery of mice subjected to acute hypoxia,
a moderate increase in the number of punished passes in the 4 plate test on mice (at a strong dose),
a reduction in the duration of the sleep induced by barbital,
the presence of stereotype movements in mice and rats, and
potentiation of the stereotypies induced by apomorphine and amphetamine in rats.

Furthermore, CRL 41 221 at strong doses shows:
an α-adrenergic stimulation component represented by a decrease in the ptosis induced by reserpine, mydriasis and salivation in mice and rats;
a reduction in the aggressiveness and (he time taken for convulsions and death to occur following asphyxiant anoxia caused by a curarizing agent; and
a reduction in the convulsant effects of electric shock.

CRL 41 221 therefore behaves as a substance possessing antidepressant properties with a large stimulant component.

III. Immunological Study

The immunological tests show that CRL 41 221 has an immunomodulating effect and increases the cellular immunity.

G TESTS RELATING TO CRL 41 222 (PRODUCT OF EXAMPLE 7)

I. Cardiovascular Study

When administered intraduodenally to 4 anesthetized dogs, CRL 41 222 causes a substantial and regular increase in the femoral and vertebral flows. The effect is proportional to the dose. This increase in the flows-is accompanied by tachycardia. A hypotensive action appears at 20 mg/kg as a drop in the diastolic blood pressure. The rectal temperature and skin temperature rise. Respiratory stimulation is observed in all the animals.

CRL 41 222 moderately increases the hypertension induced by norepinephrine, without modifying the effects of isoprenaline. Propanolol, injected at the end of the experiment, shows that CRL 41 222 acts by stimulating the $\beta$-cardiac and vascular receptors.

II. Neuropsychopharmacological Study

The tests undertaken according to the procedures described above for CRL 41 153 show that CRL 41 222 has
   antidepressant effects:
      antagonism of the hypothermia induced by apomorphine, reserpine and oxotremorine, and
      a reduction in the period of immobility due to "despair";
   stimulant effects:
      excitation in mice and rats, with the presence of stereotype movements,
      potentiation of the stereotypies induced by apomorphine and amphetamine,
      distinct antagonism of the sleep induced by barbital, and
      an increase in the motor activity, improvement in the motor recovery of mice whose motility has been depressed following a brief period in a reduced-pressure enclosure, and resumption in the motor activity of mice accustomed to their enclosure; and
   peripheral $\alpha$-adrenergic stimulant effects:
      mydriasis,
      salivation and lacrimation,
      antagonism of the ptosis induced by reserpine, and
      antagonism of the trembling induced by oxotremorine.

CRL 41 222 therefore behaves as a substance possessing antidepressant, stimulant and arousing properties. Its $LD_{50}$ in male mice is 87 mg/kg, administered intraperitoneally.

III. CLINICAL STUDY

In humans, CRL 41 222 was shown to be a good peripheral vasodilator at a daily dose of $2 \times 10$ mg in the form of tablets or gelatine capsules each containing 10 mg of CRL 41 222, taken twice a day.

H. TESTS RELATING TO CRL 41 225 (PRODUCT OF EXAMPLE 8)

The neuropsychopharmacal tests undertaken according to the procedures described above for CRL 41 153 show that CRL 41 225 has
   antidepressant effects:
      antagonism of the hypothermia induced by apomorphine, reserpine and oxotremorine, and
      a decrease in the period of immobility due to "despair"; and
   stimulant effects:
      excitation with hyperreactivity in mice and rats,
      an increase in the spontaneous motor activity of mice, resumption in the motor activity of mice accustomed to their enclosure, and improvement in the motor recovery of mice whose motility has been depressed by a brief period in a reduced-pressure enclosure,
      an increase in the number of punished passes in the 4 plate test on mice,
      a reduction in the duration of the sleep induced by barbital,
      the presence of stereotype movements in mice and rats, and
      potentiation of the stereotypies induced by amphetamine and apomorphine in rats.
   Furthermore, CRL 41 225 shows:
      a decrease in the intensity of the trembling caused by oxotremorine,
      an $\alpha$-adrenergic stimulation component represented by a decrease in the ptosis induced by reserpine in mice and, at strong doses, by a reduction in the mydriasis and salivation,
      a decrease in the time taken for convulsions and death to occur following asphyxiant anoxia caused by a curarizing agent in mice,
      at strong doses, a decrease in the number of fights in the aggressiveness test on mice, and
      at strong doses, a decrease in the convulsant effects of electric shock.

Moreover, in addition to the antidepressant and stimulant properties, it is found that CRL 41 225 has beneficial vasodilating properties from the clinical point of view.

I. TESTS RELATING TO CRL 41 233 (PRODUCT OF EXAMPLE 9)

I. Cardiovascular Study

When administered intraduodenally to anesthetized dogs, CRL 41 233 increases the femoral and vertebral flows as from a dose of 5 mg/kg, the tachycardiac effect appearing at 10 mg/kg. There is a large increase in the rectal temperature.

II. Neuropsychopharmacological Study

According to the results of tests undertaken using the procedures described for CRL 41 153, CRL 41 233 has
   antidepressant effects:
      antagonism of the hypothermia induced by apomorphine, reserpine and oxotremorine, and
      a decrease in the period of immobility due to "despair"; and
   stimulant effects:
      excitation with hyperreactivity in mice and rats,
      an increase in the spontaneous motor activity of mice, resumption in the motor activity of mice accustomed to their enclosure, and improvement in the motor recovery of mice whose motility has been depressed by a brief period in a reduced-pressure enclosure, a decrease in the duration of the sleep induced by barbital, the presence of stereotype movements in mice and rats, and potentiation of the stereotypies induced by amphetamine and apomorphine in rats. III. Conclusions CRL 41 233 behaves as a substance having vasodilating properties on the one hand and antidepressant and stimulant properties on the other.

J. TESTS RELATING TO CRL 41 237 (PRODUCT OF EXAMPLE 10)

I. Cardiovascular Study

When administered intraduodenally to an anesthetized dog, CRL 41 237 is shown to have a slight tachycardiac effect at 20 mg/kg. No action was observed on the blood pressure, the femoral flow and the vertebral flow by intraduodenal administration. On the other hand, by intravenous administration, an additional dose of 10 mg/kg of CRL 41 237 caused an increase in the femoral flow. The rectal temperature rises gradually and there is a large increase in the skin temperature.

CRL 45 237 does not modify the effects of isoprenaline but distinctly increases the hypertension induced by norepinephrine.

II. Neuropsyhopharmacological Study

The neuropsychopharmacological tests undertaken according to the procedures described above for CRL 41 153 show that CRL 41 237 has antidepressant effects:
antagonism of the hypothermia induced by apomorphine, reserpine and oxotremorine, and
a reduction in the period of immobility due to "despair";

stimulant effects:
excitation with hyperreactivity in mice and rats,
an increase in the spontaneous motor activity of mice, resumption in the motor activity of mice accustomed to their enclosure, and improvement in the motor recovery of mice whose motility has been depressed by a brief period in a reduced-pressure enclosure,
a reduction in the duration of the sleep induced by barbital,
the presence of stereotype movements in mice and rats, and
potentiation of the stereotypies induced by amphetamine and apomorphine in rats; and effects showing peripheral α-adrenergic stimulation:
mydriasis,
exophthalmos,
antagonism of the ptosis induced by reserpine, and
antagonism of the trembling induced by oxotremorine.

III. Immunological Study

CRL 41 237 has a strong activity according to the abovementioned test for cells forming lysis areas, at a dose of 100 mg/kg, administered orally, and a weaker activity on the abovementioned delayed hypersensitivity reaction to red blood corpuscles of sheep, at doses of 0.1 mg/kg to 10 mg/kg, administered orally.

IV. Clinical Study

In man, good results were obtained by oral administration in the treatment of depressions at a daily dose of !0 mg of CRL 41 237.

K. TESTS RELATING TO CRL 41 241 (PRODUCT OF EXAMPLE 11)

The neuropsychopharmacological tests undertaken according to the procedures described above for CRL 41 153 show that CRL 41 241 has antidepressant effects:
antagonism of the hypothermia induced by apomorphine, reserpine and oxotremorine, and
a reduction in the Period of immobility due to "despair"; and stimulant effects:
excitation with hyperactivity in mice and rats,
an increase in the spontaneous motor activity of mice, resumption in the motor activity of mice accustomed to their enclosure, and improvement in the motor recovery of mice whose motility has been depressed by a brief period in a reduced-pressure enclosure,
a moderate increase in the number of punished passes in the 4 plate test on mice (at high doses),
a reduction in the duration of the sleep induced by barbital,
the presence of stereotype movements in mice and rats, and
potentiation of the stereotypies induced by amphetamine and apomorphine in rats.

Furthermore, at strong doses, CRL 41 241 shows:
an α-adrenergic stimulation component represented by a decrease in the ptosis induced by reserpine, and moderate mydriasis in mice and rats,
total antagonism of the convulsant effect of electric shock, and
a very distinct reduction in the intensity of the trembling due to oxotremorine.

CRL 41 241 therefore behaves as a substance possessing an antidepressant-type effect with a large stimulant component.

L. TESTS RELATING TO CRL 41 243 (PRODUCT OF EXAMPLE 12)

The neuropsychopharmacological study shows that CRL 41 243 has modest antidepressant effects and moderate sedative effects (as distinct from the compounds according to the invention taken as a whole) and that, paradoxically, CRL 41 243 at strong doses reduces the duration of the sleep induced by barbital.

M. TESTS RELATING TO CRL 41 246 (PRODUCT OF EXAMPLE 13)

The neuropsychopharmacological tests undertaken according to the procedures described above for CRL 41 153 show that CRL 41 246 has antidepressant effects:
antagonism of the hypothermia induced by apomorphine, reserpine and oxotremorine, and
a reduction in the period of immobility due to "despair";

stimulant effects:
excitation with hyperreactivity in mice and rats,
an increase in the spontaneous motor activity of mice, resumption in the motor activity of mice accustomed to their enclosure, and improvement in the motor recovery of mice whose motility has been depressed by a brief period in a reduced-pressure enclosure, a reduction in the duration of the sleep induced by barbital, the presence of stereotype movements in mice and rats, and potentiation of the stereotypies induced by amphetamine and apomorphine in rats; and α-adrenergic stimulant effects:
mydriasis,
salivation,
antagonism of the ptosis induced by reserpine, and
antagonism of the trembling induced by oxotremorine.

COMPARATIVE ASSAYS

The compounds according to the invention were teratogenically compared with prior art compounds listed in Table A below which were prepared according to (i) the prior art teaching or (ii) the method (variant A) disclosed hereinabove.

The protocol used comprised administering to gravid White New Zealand female rabbits (weighing each about 2900–3000 grams before gestation) a daily dose of 0 (batch of control animals), 5,10 or 50 mg/kg of each product to be tested by gastrogavage from day 5 to day 18 of gestation, then carrying out a cesarean operation on day 29 of gestation in order to enumerate:

(i) the total number of foestuses, and (ii) the total number of foestuses presenting at least one malformation.

To appreciate the results of such a protocol it must be noted that natural malformations may occur. Statistically, the percentage of foetuses presenting at least one malformation in any control batch of gravid White New Zealand female rabbits is lower than or equal to 1.5% with respect to the total number of foetuses. The results that which were obtained according to said protocol are given in Table B hereinafter.

To be precise in this protocol a malformation comprises at least one of the following cases: articular limb blocade, anorous foetus, deviated tail, shorter tail, skull deformation, exemcephalia.

TABLE A $$\text{Y} \underset{\text{Z}}{\overset{\text{X}}{\diagup\!\!\!\bigcirc\!\!\!\diagdown}} \text{—CO-Alk-NR}_1\text{R}_2\text{.2HCl}$$

| PRODUCT | X | Y | Z | NR₁R₂ | Alk |
|---|---|---|---|---|---|
| A 1 (a) | 4-NH$_2$ | H | H | NHCH(CH$_3$)$_2$ | CH$_2$CH$_2$CH$_2$ |
| A 2 (a) | 4-NH$_2$ | H | H | NHC(CH$_3$)$_3$ | CH$_2$CH$_2$CH$_2$ |
| A 3 (a, b) | 4-NH$_2$ | 3-Cl | 5-Cl | NHCH(CH$_3$)$_2$ | CH$_2$CH$_2$CH$_2$ |
| A 4 (c) | 4-NH$_2$ | H | H | morpholino | CH$_2$CH$_2$CH$_2$ |
| A 5 (a) | 4-NH$_2$ | H | H | piperidino | CH$_2$CH$_2$CH$_2$ |
| A 6 (a) | 4-NH$_2$ | H | H | pyrrolidino | CH$_2$CH$_2$CH$_2$ |
| A 7 (d) | 4-NH$_2$ | H | H | NHCH$_2$CH$_3$ | CH$_2$CH$_2$ |
| A 8 (d) | 4-NH$_2$ | H | H | N(CH$_3$)$_2$ | CH$_2$CH$_2$ |
| A 9 (d) | 4-NH$_2$ | H | H | morpholino (N–O ring) | CH$_2$CH$_2$ |
| A 10 (d) | 4-NH$_2$ | H | H | piperidino (N ring) | CH$_2$CH$_2$ |
| A 11 (d, e) | 4-NH$_2$ | H | H | N-methylpiperazino (N–N–CH$_3$ ring) | CH$_2$CH$_2$ |
| A 12 (d) | 4-NH$_2$ | H | H | NH-cyclopropyl | CH$_2$CH$_2$ |
| A 13 (d) | 4-NH$_2$ | H | H | thiomorpholino (N–S ring) | CH$_2$CH$_2$ |
| A 14 (g) | 4-NH$_2$ | H | H | NHCH(CH$_3$)$_2$ | CH$_2$ |
| A 15 (g) | 3-NH$_2$ | H | H | NHCH(CH$_3$)$_2$ | CH$_2$ |
| A 16 (f) | 4-NH$_2$ | H | H | morpholino | CH$_2$ |
| A 17 (g) | 3-NH$_2$ | H | H | morpholino | CH$_2$ |
| A 18 (g) | 4-NH$_2$ | H | H | piperidino | CH$_2$ |
| A 19 (g) | 3-NH$_2$ | H | H | piperidino | CH$_2$ |
| A 20 (g) | 4-NH$_2$ | H | H | pyrrolidino | CH$_2$ |
| A 21 (g) | 3-NH$_2$ | H | H | pyrrolidino | CH$_2$ |

TABLE A-continued

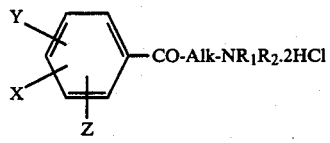

| PRODUCT | X | Y | Z | NR₁R₂ | Alk |
|---|---|---|---|---|---|
| A 22 (b, h) | 4-NH$_2$ | 3-Br | H | 2-ethylpiperidino | CH(CH$_3$) |

Notes
(a) according to the teaching of US-A-3 772 275
(b) monohydrochloride
(c) disclosed in US-A-3 772 275
(d) according to the combined teaching of US-A-3 772 275 and US-A-4 282 206
(e) trihydrochloride
(f) disclosed in US-A-4 282 206
(g) according to the teaching of US-A-4 282 206
(h) disclosed in GB-A-1 180 890

TABLE B

| Product | Code No | Dose mg/kg | Total gravid females (a) | Total foetuses (b) | Affected foetuses (c) number | % |
|---|---|---|---|---|---|---|
| Control batch | — | 0 | 18 | 177 | 2 | 1.12 |
| Ex 1 | CRL 41 153 | 5 | 9 | 90 | 0 | 0 |
| Ex 1 | CRL 41 153 | 10 | 9 | 88 | 1 | 1.13 (d) |
| Ex 1 | CRL 41 153 | 50 | 10 | 93 | 0 | 0 |
| Ex 2 | CRL 41 178 | 5 | 10 | 90 | 1 | 1.11 |
| Ex 2 | CRL 41 178 | 10 | 8 | 83 | 1 | 1.20 (d) |
| Ex 2 | CRL 41 178 | 50 | 9 | 92 | 1 | 1.10 |
| Ex 3 | CRL 41 194 | 5 | 11 | 95 | 1 | 1.10 |
| Ex 3 | CRL 41 194 | 10 | 11 | 91 | 0 | 0 |
| Ex 4 | CRL 41 213 | 0 | 8 | 84 | 1 | 1.19 (d) |
| Ex 5 | CRL 41 218 | 50 | 8 | 79 | 1 | 1.26 (d) |
| Ex 6 | CRL 41 221 | 5 | 10 | 91 | 1 | 1.11 (d) |
| Ex 6 | CRL 41 221 | 10 | 9 | 87 | 1 | 1.14 (d) |
| Ex 7 | CRL 41 222 | 5 | 9 | 85 | 1 | 1.29 (d) |
| Ex 7 | CRL 41 222 | 10 | 10 | 92 | 0 | 0 |
| Ex 8 | CRL 41 225 | 5 | 10 | 91 | 0 | 0 |
| Ex 8 | CRL 41 225 | 10 | 11 | 95 | 0 | 0 |
| Ex 9 | CRL 41 233 | 5 | 10 | 89 | 1 | 1.12 (d) |
| Ex 9 | CRL 41 233 | 10 | 8 | 85 | 0 | 0 |
| Ex 10 | CRL 41 237 | 5 | 9 | 91 | 0 | 0 |
| Ex 10 | CRL 41 237 | 10 | 10 | 96 | 1 | 1.04 (d) |
| Ex 10 | CRL 41 237 | 50 | 9 | 88 | 1 | 1.13 (d) |
| Ex 11 | CRL 41 241 | 10 | 10 | 88 | 0 | 0 |
| Ex 12 | CRL 41 243 | 50 | 9 | 87 | 0 | 0 |
| Ex 13 | CRL 41 246 | 5 | 9 | 89 | 1 | 1.12 |
| Ex 13 | CRL 41 246 | 10 | 10 | 94 | 0 | 0 |
| Ex 14 | CRL 41 248 | 10 | 11 | 93 | 1 | 1.07 (d) |
| Ex 15 | CRL 41 255 | 10 | 9 | 89 | 1 | 1.12 (d) |
| Ex 16 | CRL 41 260 | 10 | 8 | 87 | 1 | 1.14 (d) |
| Ex 17 | CRL 41 263 | 10 | 10 | 92 | 0 | 0 |
| Ex 18 | CRL 41 268 | 10 | 9 | 91 | 1 | 1.11 (d) |
| Ex 19 | CRL 41 278 | 10 | 9 | 92 | 1 | 1.08 (d) |
| A 1 | — | 10 | 9 | 87 | 4 | 4.59 (e) |
| A 2 | — | 10 | 8 | 85 | 4 | 4.70 (e) |
| A 3 | — | 10 | 8 | 82 | 5 | 6.09 (e) |
| A 5 | — | 5 | 8 | 81 | 3 | 3.70 (e) |
| A 5 | — | 10 | 9 | 87 | 4 | 4.59 (e) |
| A 6 | — | 5 | 8 | 89 | 0 | 0 |
| A 6 | — | 10 | 8 | 86 | 5 | 5.81 (e) |
| A 7 | — | 5 | 8 | 80 | 1 | 1.25 (d) |
| A 7 | — | 10 | 8 | 79 | 4 | 5.06 (e) |
| A 8 | — | 10 | 9 | 81 | 5 | 6.17 (e) |
| A 9 | — | 5 | 9 | 86 | 1 | 1.16 (d) |
| A 9 | — | 10 | 10 | 94 | 0 | 0 |
| A 9 | — | 50 | 8 | 82 | 6 | 7.31 (e) |
| A 10 | — | 10 | 8 | 78 | 4 | 5.12 (e) |
| A 11 | — | 10 | 9 | 80 | 6 | 7.50 (e) |
| A 12 | — | 5 | 8 | 75 | 2 | 2.66 (e) |
| A 13 | — | 10 | 7 | 43 (f) | 12 | 27.90 |
| A 14 | — | 10 | 8 | 76 | 3 | 3.94 (l) |
| A 15 | — | 10 | 7 | 52 (f) | 14 | 26.92 |
| A 16 | — | 5 | 9 | 81 | 3 | 3.70 (e) |
| A 16 | — | 10 | 7 | 50 (f) | 13 | 26.0 |
| A 17 | — | 5 | 8 | 77 | 2 | 2.59 (e) |
| A 17 | — | 10 | 7 | 46 (f) | 11 | 23.91 |
| A 18 | — | 5 | 8 | 80 | 4 | 5.0 (e) |
| A 18 | — | 10 | 8 | 51 (f) | 10 | 19.60 |

TABLE B-continued

| Product | Code No | Dose mg/kg | Total gravid females (a) | Total foetuses (b) | Affected foetuses (c) number | % |
|---|---|---|---|---|---|---|
| A 19 | — | 10 | 7 | 62 | 3 | 4.83 (e) |
| A 20 | — | 10 | 8 | 74 | 5 | 8.10 (e) |
| A 21 | — | 10 | 9 | 78 | 4 | 5.12 (e) |
| A 22 | — | 10 | 7 | 46 (f) | 13 | 28.26 |

Notes
(a): Total number of gravid female rabbits; day 1 of gestation is the day on which a male rabbit is placed in the female's cage.
(b): Total number of live foetuses.
(c): Live foetuses presenting malformation; the percentage is given with respect to the total number of live foetuses.
(d): Lower than the statistically upper "normal" limit of 1.5%.
(e): Higher than the statistically upper "normal" limit of 1.5%.
(f): Lower than the average 8–10 live foetuses per litter as observed from the other results of Table B.

The data of Table B clearly show that, unlike prior art products, the compounds according to the invention are not teratogenically harmful.

STARTING MATERIALS

The compounds of the formula II (variant A) cited hereinabove are obtained according to the following reaction $$ArCOCH(CH_3)Hal + HNR_1R_2 \rightarrow \quad II$$

wherein Ar represents an acetylaminophenyl group of the formula

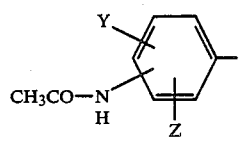

in which Y, Z $R_1$ and $R_2$ are as above defined; and Hal represents a halogen atom, in particular Cl or Br, said reaction being carried out for at least 0.5 h at a temperature comprised 15° C. and the reflux temperature of the reaction medium, as disclosed in co-pending U.S. patent application Ser. No. 038,981 of Apr. 16, 1987, now U.S. Pat. No. 4,877,812, which was a continuation application of a previous U.S. patent application Ser. No. 660,285 of Oct. 12, 1984, now abandoned.

What is claimed is:

1. A 1-(aminophenyl)-2-aminopropanone compound selected from the group consisting of:
   (a) compounds of the formula

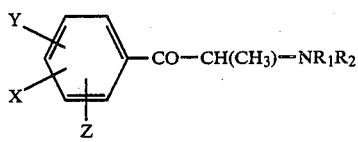

wherein
   X is 3-$NH_2$ or 4-$NH_2$,
   Y and Z are each H,
   $R_1$ is $C_1$-$C_4$ alkyl or $C_3$-$C_6$ cycloalkyl, and
   $R_2$ is H or $C_1$-$C_4$ alkyl;
   (b) 1-(amino-halogenophenyl)-2-aminopropanone compounds of the formula I wherein
   X is 4-$NH_2$,
   Y is 3-Cl,
   Z is H or 5-Cl,
   $R_1$ is $CH(CH_3)_2$, and
   $R_2$ is H; and
   (c) nontoxic acid addition salts thereof.

2. A compound according to claim 1, which is 1-(4-amino-3,5-dichlorophenyl)-2-isopropylaminopropanone or one of its non-toxic addition salts.

3. A compound according to claim 1, which is 1-(4-aminophenyl)-2-tert.-butylaminopropanone or one of its non-toxic addition salts.

4. A compound according to claim 1, which is 1-(4-amino- 3-chlorophenyl-2-isopropylaminopropanone or one of its non toxic addition salts.

5. A compound according to claim 1, which is 1-(4-aminophenyl)-2-cyclopropylaminopropanone or one of its non-toxic addition salts.

6. A therapeutic composition comprising, in association with a physiologically acceptable excipient, a pharmaceutically effective quantity of a 1-(aminophenyl)-2-amino-propanone compound according to claim 1.

7. A method for the treatment of depression, which comprises adminstering, to a patient in need of such a treatment, a pharmaceutically effective quantity of a compound of the formula I according to claim 1 or one of its non-toxic addition salts.

* * * * *